United States Patent [19]

Takahashi et al.

[11] Patent Number: 4,832,444
[45] Date of Patent: May 23, 1989

[54] METHOD AND APPARATUS FOR TRANSMITTING LIGHT

[75] Inventors: Kenichi Takahashi; Noriyuki Yoshida, both of Osaka, Japan

[73] Assignee: Sumitomo Electric Industries, Ltd., Osaka, Japan

[21] Appl. No.: 870,356

[22] Filed: Jun. 4, 1986

[30] Foreign Application Priority Data

Jun. 17, 1985 [JP] Japan .................................. 60-131608
Jul. 10, 1985 [JP] Japan .................................. 60-151623

[51] Int. Cl.⁴ .............................................. G02B 23/26
[52] U.S. Cl. .................................. 350/96.26; 350/96.23; 128/6
[58] Field of Search ................. 350/96.1, 96.23, 96.24, 350/96.25, 96.26, 96.29, 96.30, 96.33, 96.34; 128/4, 6, 7, 8, 9

[56] References Cited

U.S. PATENT DOCUMENTS

| 3,261,351 | 7/1966 | Wallace | 350/96.26 X |
|---|---|---|---|
| 3,674,010 | 7/1972 | Falenks | 128/2 R |
| 3,830,225 | 8/1974 | Shinnick | 128/2 B |
| 3,843,865 | 10/1974 | Nath | 219/121 L |
| 4,010,345 | 3/1977 | Banas et al. | 219/121 L |
| 4,273,109 | 1/1981 | Enderby | 350/96.26 X |
| 4,427,000 | 1/1984 | Ueda | 128/6 |
| 4,509,507 | 4/1985 | Yabe | 128/4 |
| 4,640,575 | 2/1987 | Dumas | 350/96.1 X |
| 4,667,229 | 5/1987 | Cooper et al. | 128/6 X |
| 4,669,819 | 6/1987 | Hengst et al. | 350/96.26 X |

FOREIGN PATENT DOCUMENTS 0044018  1/1982  European Pat. Off. ............. 128/6

Primary Examiner—John D. Lee
Assistant Examiner—John Ngo
Attorney, Agent, or Firm—Cushman, Darby & Cushman

[57] ABSTRACT

A light transmission apparatus in which light from a laser may be transmitted through an optical conducter. Dry air may also be pumped through the optic conducter to remove matter from the vicinity of the light emitting end. A cover which is formed of a shape memory alloy is provided at the light emitting end of the conductor to open at a high temperature in response to incident light and close at a low temperature when the light stops.

31 Claims, 3 Drawing Sheets

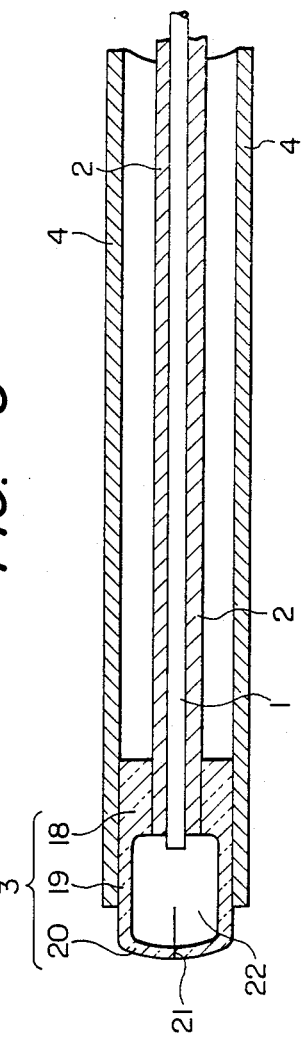
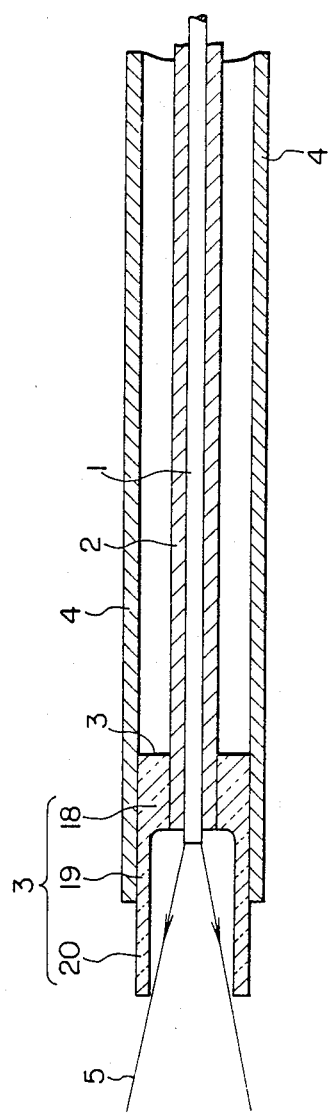

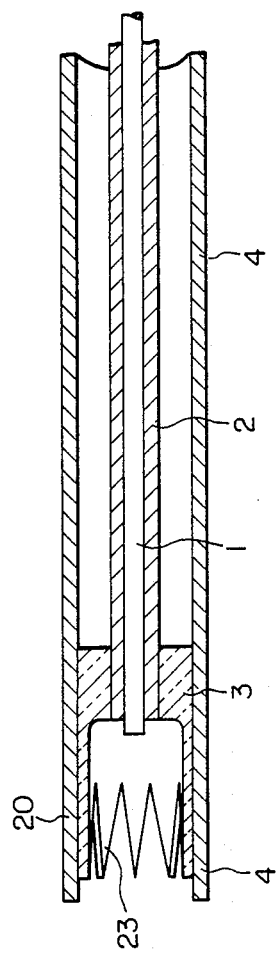
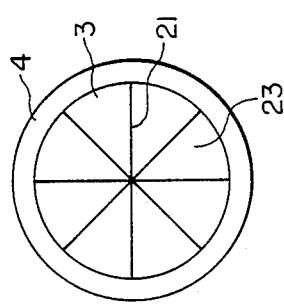
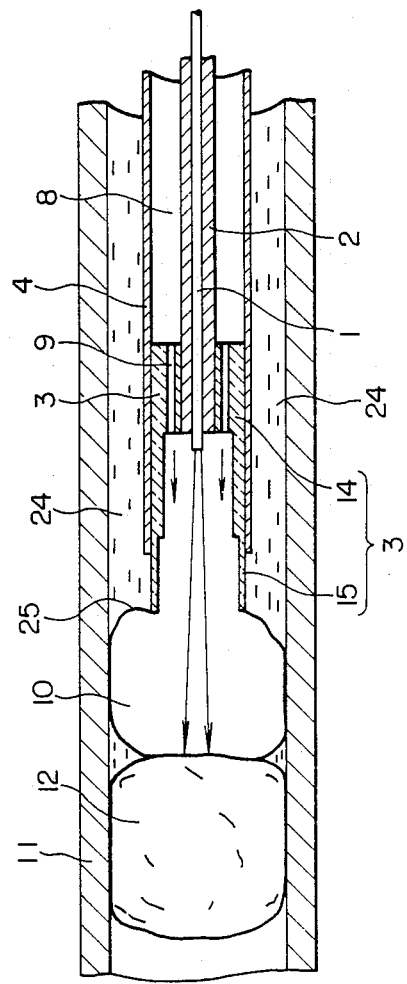
FIG. 6
FIG. 8
FIG. 7

METHOD AND APPARATUS FOR TRANSMITTING LIGHT

BACKGROUND OF THE INVENTION

1. Field of the Invention

The present invention relates to an improvement in an optical fiber system for transmitting a laser beam.

2. Description of the Prior Art

Recently, power transmitting optical fibers have become widely used in industry, medicine and the like. The term "power" includes high laser power. Typical lasers include carbon dioxide lasers, YAG lasers, Ar lasers and the like. YAG lasers, Ar lasers and the like, can transmit through a quartz glass fiber. However, light from a carbon dioxide laser can not be transmitted through a quartz fiber because of its long wave length. Although it can be transmitted by means of a mirror, the structure of articulation is so complicated to make use difficult. However, crystalline fibers of silver halide, thallium halide, and alkali halide can transmit the light of the carbon dioxide laser.

Advantages in light power transmission by means of optical fibers are such that light can be conducted into even a narrow space and along a complicated path having many bent portions to irradiate any object. This is because an optical fiber has superior characteristics such as small diameter, flexibility and so on.

Although one end of the optical fiber is connected with a laser source, the other end is often exposed because it is necessary to emit a laser beam therefrom toward an object to be irradiated with the laser beam. However, the end from which the laser beam is emitted (hereinafter simply referred to as "a light-emitting end"), is often inserted into a narrow space, into a space having many bent portions, or into a space filled with a liquid or a solid, so that the light-emitting end is apt to be damaged. Foreign matter, such as dust, drops of water, blood, or the like, may adhere on the light-emitting end of an optical fiber used for power-transmitting a laser beam, depending on the environment in which the optical fiber is used.

If a laser beam is passed through an optical fiber with foreign matter adhered on its light-emitting end, the foreign matter is heated by the laser beam and sometimes burnt and stuck on the end surface of the optical fiber. If this happens, transmission quality deteriorates, and the temperature sharply rises as the laser beam energy is absorbed by the foreign matter, damaging the light-emitting end of the optical fiber.

Conventionally, an opening/closing cover has been provided at the light-emitting end of an optical fiber to prevent such accidents. The cover is opened only when a laser beam is emitted and closed when no laser beam is being emitted. Thus, the light-emitting end of the optical fiber is being protected by the cover when no laser beam is emitted. However, the laser beam per se has no power to prevent dust, blood, drops of water, or the like, from adhering onto the light-emitting end. When the light-emitting end of the optical fiber is put in an environment containing liquid, such as water drops, blood, or the like, the liquid may adhere to the light-emitting end when the protecting cover is opened during emission. This deteriorates the transmittivity at the end surface to extremely reduce the treating capability of the laser beam. Further, the light-emitting end may be sometimes broken because the end surface is sharply heated. There are two kinds of opening/closing mechanisms, one being of the type provided at the forward end of an optical fiber and the other being of the type provided in the back of an optical fiber and controlled remotely.

An opening/closing mechanism at the forward end of an optical fiber is provided with a motor, a reduction gear, gearing, and so on, attached at that end to open and close the cover by the forward and backward rotation of the motor. In such a cover opening/closing mechanism, it is necessary to attach a motor, a reduction gear, a gearing, and so on, at a light-emitting end of an optical fiber, so that the end of the optical fiber becomes bulky, loses flexibility and becomes heavy. Moreover, it is necessary to incorporate electrical conductive lead wires in the optical fiber as a power feeder and a signal line for the motor, so that the structure of the optical fiber becomes complicated.

Thus, if a prime mover is attached at the light-emitting end, the light-emitting end becomes heavy and bulky. Therefore a mechanism has been proposed to remotely operate the cover. In this mechanism, a motor, a reduction gear, and the like are provided not at the light-emitting end of an optical fiber but in the vicinity of the light source. A cover opening/closing portion urged in one direction by a spring and pulled in the reverse direction by a wire is provided at the forward end of the optical fiber. The motor, or the like, and the cover opening/closing portion at the forward end of the optical fiber are connected with each other by a wire extending along the optical fiber.

Thus, the mechanical structure provided at the light-emitting end of the optical fiber is reduced in size as well as in weight and becomes easier to use. The wire, however, must be provided along the fiber, so that the structure of the optical fiber becomes complicated. Also the flexibility at the intermediate portion of the optical fiber is reduced.

SUMMARY OF THE INVENTION

It is therefore an object of the present invention to provide a high laser power transmission optical fiber arranged to prevent foreign matter from adhering to and burning on the light-emitting end of the optical fiber.

It is another object of the present invention to provide a power transmission optical fiber with a cover opening/closing mechanism which has few mechanical parts so as to make failures few.

It is a further object to provide a power transmission optical fiber with a cover opening/closing mechanism at the light-emitting end of the optical fiber and arranged so as not to make the light-emitting end of the optical fiber heavy and bulky and so as not to make the structure of the optical fiber complicated, so that the flexibility of the optical fiber is not lost and that the operation is improved because the light-emitting end of the optical fiber is small in size as well as light in weight.

In the optical fiber according to the present invention, an openable/closable protecting cover is provided at the light-emitting end of the optical fiber, and a blower is provided at the light source end of the optical fiber to feed a gas to the light-emitting end along the optical fiber to remove liquid from the vicinity of the light-emitting end to thereby protect the light-emitting end.

Further, a gas pressure sensor is provided to monitor the pressure of the gas in the vicinity of the light-emitting end.

According to the present invention, the cover provided at the light-emitting end is made of a shape memory alloy so as to open and close in response to laser beam power per se.

The cover is made of such a shape memory alloy so as to store such a shape that the cover closes at low temperature and opens at high temperature.

The shape memory alloy can be transformed by the power thereof into a previously stored shape if the temperature is changed. The laser beam per se is used to change the temperature.

Upon being driven, a laser beam is emitted from the light-emitting end of the optical fiber and impinges onto an inner surface of the cover made of the shape memory alloy. Because the laser beam has large power, the temperature at the cover is raised. Storing a shape to open at a high temperature, the cover is opened as the temperature is raised.

When the laser beam is no longer emitted from the light-emitting end of the optical fiber the temperature at the cover is lowered, and the cover is closed. The temperature at the cover is lowered fairly rapidly as heat is lost due to radiation, conduction, and convection. Thus, the cover can be closed in a relatively short time after the laser beam has been extinguished.

BRIEF DESCRIPTION OF THE DRAWINGS

Referring to the drawings, the optical fiber according to the present invention will be described hereunder.

FIG. 3 is a cross-section showing the structure of the light-emitting end of the optical fiber according to the present invention, in which the cover is in the closed state.

FIG. 4 is an enlarged front view of the light-emitting end.

FIG. 5 is a cross-section showing the structure of the light-emitting end of the optical fiber, in which the cover is in the open state.

FIG. 7 is a front view of the light-emitting and opening/closing cover constituted by eight divisional members.

FIG. 8 is a longitudinal cross-section showing the state in which the forward end portion of the optical fiber is inserted into a thin pipe and is emitting a laser beam.

DETAILED DESCRIPTION OF THE DRAWINGS

Figure 1:
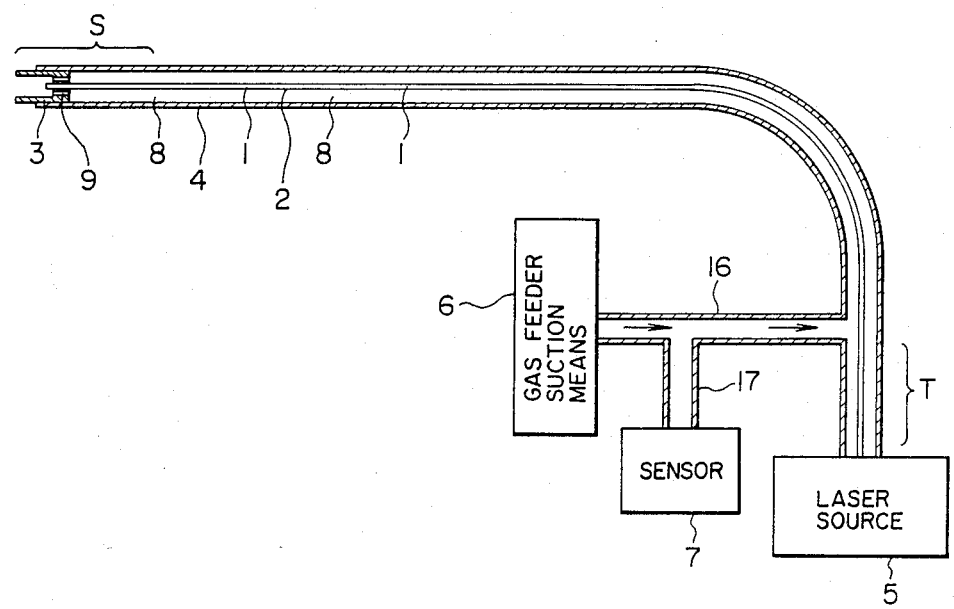
FIG. 1 is a diagram showing the whole arrangement of the optical fiber according to the present invention.

Optical conductor 1 is a member provided in the center of the optical fiber for conducting a laser beam. As described above, the optical conductor has a small diameter and sufficient flexibility to be bent as desired. In the case of a carbon dioxide laser, crystal fibers of silver halide, thallium halide, and alkali halide are used. In the case of a YAG and an Ar lasers quartz glass fibers are employed. The material is selected based on the wavelength of the laser. The whole of the optical conductor 1 is covered with a protecting inner layer 2 which is made of flexible synthetic resin. An openable/closable forward end protecting cover 3 is provided at the light-emitting end S of optical conductor 1.

The whole of the protecting inner layer 2 is surrounded by a protecting outer layer 4 such that a space is provided between the inner and outer layers so as not to lose flexibility. According to the present invention, gas pumped or sucked through the space and therefore the space is hereinafter referred to as ventilation path 8.

The other end of the optical fiber is connected with a laser source 5 which may be a carbon dioxide laser, a YAG laser, an Ar laser, or the like. The end of the optical fiber near the light source is referred to as a light source end T. According to the present invention, a blower 6 or gas feeder/suction means and a gas pressure sensor 7 are provided in the vicinity of the light source end T of the optical fiber. Pressure in the optical fiber is monitored by the sensor 7. The gas feeder/suction means 6 supplies gas to the end portion of the optical fiber, or sucks the gas if gas pressure exceeds predetermined value.

Various structures have been proposed for opening/closing the forward end protecting cover. In one of the proposed mechanisms of the type in which the cap is mechanically opened/closed, a motor as a driving source is provided in the vicinity of the light-emitting end of the optical fiber. Lead wires are passed through the protecting outer layer. There is another mechanism in which a motor is provided at the light source end of the optical fiber and the forward end protecting cover is opened/closed by a wire. The wire is passed through the protecting outer layer of the optical fiber. There is a third mechanism in which the forward end protecting cover is opened/closed by hydraulic or pneumatic pressure. A transmission line for the pressure liquid or gas is made by inserting a tube within the protecting outer layer.

In the present invention, however, a shape memory alloy is used as a mechanical forward end protecting cover.

Figure 2:
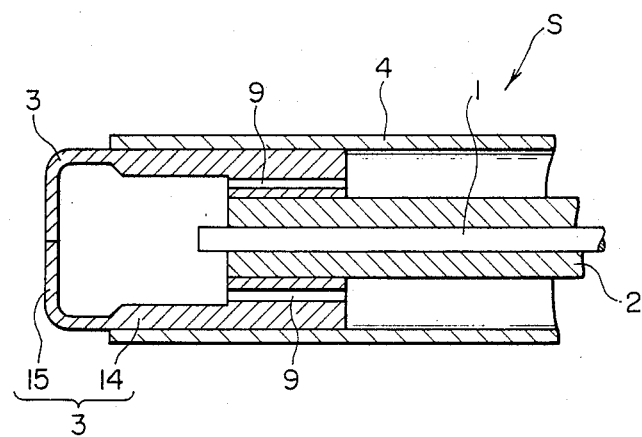
FIG. 2 is an enlarged cross-section showing a portion in the vicinity of a light-emitting end.

The gas feeder/suction means 6 and the protecting outer layer 4 are connected with each other through a connecting tube 16. The gas pressure sensor 7 and the connecting tube 16 are connected with each other through a connecting tube 17. As shown in FIG. 2, the forward end protecting cover 3 is constituted by a boss portion 14 and an opening/closing cap portion 15. Ventilation holes 9 are provided so as to axially pass through the boss portion 14. The ventilation holes 9 open into a space surrounded by the forward end protecting cover 3 to communicate with the ventilation path 8 surrounded by the protecting outer layer 4.

Shape memory alloy is an alloy having shape-restoring force on the basis of thermo-elastic martensitic transformation and reverse transformation. Here, a closed state at a low temperature and opened state at a high temperature are stored. Alloys of Ni-Ti, Cu-Sn, Cu-Zn, Cu-Al, and the like, can be used as a shape memory alloy. Each of those alloys has a stable shape which is determined depending on a temperature and can store a shape at a temperature equal to or lower than a predetermined value as well as another shape at a temperature equal to or higher than a predetermined value, so that the alloy can be changed in its shape by being heated/cooled.

For example, Ni-Ti alloy consists of Ni of 50–60% by weight and Ti of 40–50% by weight. The alloy has restoring force on the basis of thermo-elastic martensitic transformation and reverse transformation to thereby change the shape.

The temperature at which the shape transformation occurs, that is, the transformation temperature, can be adjusted by selecting the compounding ratio of the alloy. Although the Ni-Ti alloy is representative, an alloy in which Ni or Ti is partially substituted by Al, Cu, V, Zr, Cr, Mo, Fe, Co, or the like, may be used.

The light-emitting end opening/closing cover 3 is made of metal and preferably has such a shape that two divisional members are combined with each other as shown in FIG. 3 and FIG. 4. The cover 3 is provided at its root with a cylindrical attaching portion 18 for fixing the cover 3 between the inner and outer layers of the optical fiber. The inner diameter of the attaching cylindrical portion 18 is made to agree with the outer diameter of the protecting inner layer 2. The cover 3 has an intermediate cylindrical portion 19 in front of the attaching cylindrical portion 13 and an opening/closing cap portion 20 covering the front end of the optical fiber 1 in front of the intermediate cylindrical portion 19. The cap 3 is constituted by the two divisional members. A dividing line 21 appears on the front surface of the opening/closing cap portion 20.

The light-emitting end opening/closing cover 3 has an inner space 22 encircled by the intermediate cylindrical portion 19 and the opening/closing portion 20 thereof. In the drawing, the optical conductor 1 is projected a little into the inner space 22. However, the degree of projection of the conductor 1 is selective and there is no obstacle even if the respective front end surfaces of the protecting inner layer 2 and the optical conductor 1 are made even.

When a laser beam is emitted from the light-emitting end, the laser beam 5 impinges onto the back surface of the light-emitting end opening/closing cover 3. The laser beam has considerable power. A part of the laser beam is reflected and the remainder absorbed by the back surface of the cover 3. The absorbed light sharply raises the temperatures of the light-emitting end opening/closing cover. Therefore, the opening/closing cap portion 20 is opened at the dividing line 21. FIG. 5 shows the opened state.

If the rate of the reflected light is large, the respective end portions of the optical conductor 1 and the protecting inner layer 2 may be damaged by the heat. Accordingly, it is preferable to reduce the reflection factor on the back surface of the opening/closing cap portion 20. For this reason, the back surface of the opening/closing portion 20 is preferably colored black or made rough.

In this embodiment, cover 3 is constituted by two divisional members. This is possible when the cover is very thin. Even in such a shape memory alloy, it is impossible to easily change the thickness thereof, so that a distance between any two points is substantially maintained before and after transformation owing to heat. A shape memory alloy is not capable of expansion and contraction.

Thus it is advantageous to divide the opening/closing cap portion 20 into three to eight members. If the cap portion 20 is divided into eight members, eight dividing lines are formed and the central angle of each divisional member is 45 degrees. The opening/closing cap portion 20 constituted by the collection of the thus finely divided members can be smoothly opened/closed without requiring any circumferential elasticity.

It is possible to increase the number of the divisional members, for example, to divide the cap portion 20 into 9 to 20 members. In this case, sharp divisional members stand outwardly side by side in the opened state of the cap portion, so that there is a danger that the divisional members may injure circumferential portions when they touch the latter. For example, if the outer layer 2 is extended to cover the respective forward ends of the divisional members of the cover portion in the opened state of the cap portion as shown in FIG. 6, the divisional members can be prevented from injuring the circumferential portions.

The opened state of the cap portion is maintained as long as a laser beam is emitted, because the laser beam continues to heat the cover. If the cover has been opened, the cover is little irradiated with the light so that the cover begins to cool. If the temperature of the cover is lowered to a value equal to or lower than the transformation temperature, the cover is closed.

When the light hits directly again on the thus closed cover, the cover is reopened. This oscillating phenomenon is undesirable.

Accordingly, it is desirable to arrange that a part of the light impinges on a part of the divisional members of the cover even in the opened state of the cap portion. The heat generated in the part of the divisional members of the cover is immediately transmitted all over the cover to keep the temperature at a value equal to or higher than the transformation temperature.

Although it is desirable to use Ar or $N_2$ gas as the gas to be fed from the blower into the inside of the optical fiber, air may be used according to circumstances. The humidity of the blow gas must be sufficiently low. The relative humidity must be equal to or lower than 40% and most preferably 0%. If a gas having high humidity is fed, water is condensed in the vicinity of the light-emitting end of the optical fiber. In the case of an optical fiber for transmitting a laser beam of a large power, a part of the laser beam is absorbed into the water drops to raise the temperature thereat. Therefore, damage may result at the output terminal of the optical fiber. Accordingly, low humidity is desired to prevent such accidents.

The pressure of the gas to be fed by the blower is sufficient if it can remove a liquid or the like at the light-emitting end. High pressure is undesirable because the quantity of the gas coming out of the light-emitting end to the outside increases. Accordingly, it is preferable to select as the pressure a value as low as possible within a range where the liquid or the like can be removed. Depending on the pressure loss in the ventilation path of the optical fiber, the pressure is preferably selected to a value equal to or less than 2 $Kg/cm^2$ when it is monitored by a gas pressure sensor 7 at the light source end. The pressure is preferably selected to be 1.01–1.2 $Kg/cm^2$.

When the laser source 5 is turned off, no laser beam is generated. The protecting cover 3 at the forward end of the optical fiber closes. The blower 6 is driven. Although the pressure in the ventilation path 8 inside the protecting outer layer 4 rises, the protecting cover 3 is in the closed state so that the gas does not come out from the light-emitting end to the outside. This state is shown in FIGS. 2 and 3.

Assume now that the laser source 5 is driven. The laser beam enters the optical conductor 1 through the light source end T thereof and passes therethrough. The light coming out of the light-emitting end impinges on the back surface of the opening/closing cap portion 15 of the forward end protecting cover 3.

The opening/closing cap portion 15 is heated. Storing a shape so as to open at a high temperature, the cap portion 15 soon opens. After that, the laser beam goes straight ahead to impinge onto an object to be irradiated located in front of the fiber light-emitting end. At the same time, the gas fed from the air flow hole is pumped forward. In the case where the fiber light-emitting end is surrounded by a liquid or fluid body of high viscosity, the gas prevents the liquid or a solid body from approaching the fiber light-emitting end.

FIG. 8 illustrates a further embodiment in which the forward end of the optical fiber is inserted into a thin pipe filled with a liquid 24 or the like and a laser beam is irradiated onto workpiece 12 from the light-emitting end.

Although the boundary surface 25 between fed gas 10 and the liquid 24 is illustrated to be spherical, it may take any of various shapes in practical cases and the shape per se is unstable. If the viscosity of the liquid 20 is made higher, the boundary surface 25 becomes more stable.

The fact that the forward end protecting cover 3 is opened can be detected by a gas pressure sensor 7. A sharp reduction in the gas pressure P indicates that the forward end protecting cover 3 has been opened.

Upon completion of working, the laser source 5 is turned off. The generation of the laser beam is stopped. The forward end protecting cover is reduced in temperature to thereby return to the original closed state. During this operation, the gas is fed continuously from the gas feeder/suction means 6. The circumferential liquid or the like is prevented by pumping of the gas from entering the forward end of the optical conductor 1. The forward end of the optical conductor 1 is thus kept clean.

Closing of the forward end protecting cover 3 is detected by the immediate increase of the pressure at the gas pressure sensor 7. In this example, the opening/closing cap portion 15 of the forward end protecting cover 3 is divided into two members. In the case where it is difficult to open/close the shape memory alloy with two members, the cap portion 15 may be divided into 3 to 10 members.

After termination of working by the laser beam, further supply of unnecessary gas can be stopped so that the laser beam can be safely used without unnecessary gas being pumped into the body of the apparatus.

The optical fiber can be used for:

(1) Laser beam working machines in the industrial field (laser cutting, heat-treating, welding); and (2) Laser treating medical machines (laser surgical knife, laser coagulator). Particularly, the optical fiber can be suitably used where a miniaturized thin optical fiber is required.

Example I

A quartz glass fiber provided with a core as an optical conductor having a diameter of 500 $\mu$m was used.

A YAG laser having a wave length of 1.06 $\mu$m and an Ar laser having wave length of 0.56 $\mu$m can be used as a laser source for a quartz glass fiber. Here, a YAG laser having an output of 100 W was used as a light source.

The forward end protecting cover was made of a shape memory alloy consisting of Ni of 50–60% by weight and Ti of 40–50% by weight. The cover was to store a closed state at a low temperature and an opened state at a high temperature.

It is preferable not to make the back surface of the cover a mirror surface. In the case of the mirror surface, the fiber end was injured by the reflected light even in the case in which the output of the laser beam was 10 W (the output of the light source.)

Next, the back surface of the cover was made rough. The roughness was selected to be $R_{max}=10\mu$. $R_{max}$ is the maximum value of the convex-concave of the surface. Then, the output end of the optical fiber was not injured by the light reflected by the cover even when a laser beam having an output of 100 W was used.

When the laser beam was emitted, the cover was opened by heat, and when the laser beam was stopped, the cover returned again to the closed state.

As shown in FIG. 10, the forward end of the optical fiber was inserted into a thin pipe filled with a sticky liquid. As the gas to be fed, air having relative humidity not higher than 40% was used.

In the thus arranged apparatus, the YAG laser was driven. The forward end protecting cover made of the shape memory alloy was opened by the laser beam.

The pressure of the fed gas was 1.01–1.2 kg/cm$^2$.

A gaseous space in which the laser beam was little absorbed was formed in front of the light-emitting end of the optical fiber by the fed gas. The workpiece was worked by the laser beam. The optical fiber then drawn out. When the light-emitting end of the optical fiber was investigated, there was no marks to which a liquid was adhered.

Example II

A silver halide fiber provided with a core as an optical conductor having a diameter of 1000 $\mu$m was used.

A carbon dioxide laser having an output of 50 W and a wave length of 10.6 $\mu$m was used as the laser beam source.

As the optical fiber, it is possible to use any other infrared optical fibers, optical fibers of thallium halide such as KRS-5, and optical fibers of alkali metal halide such as cesium bromide.

As shown in FIGS. 2 and 4, the forward end protecting cover was made of a shape memory alloy and arranged to have an opening/closing cap portion constituted by two divisional members.

As the shape memory alloy, a Ni-Ti alloy was used.

Also in this case, the inner surface of the cover was made rough. In the case where the inner surface was a mirror surface, the forward end of the optical fiber was injured even if the laser power was 10 W.

Dry air having humidity not higher than 40% came from the blower.

There was a plug made of plastic and the forward end of the optical fiber was inserted into a thin pipe filled with water, as shown in FIG. 8.

The opening/closing cap portion of the protecting cover could be opened owing to the irradiation by the laser beam. A space in which a liquid had been removed could be maintained in the thin pipe by air. A work could be worked by irradiating with the laser beam. At that time, the pressure of the gas was 1.01–1.2 kg/cm$^2$.

What is claimed is:

1. A light transmission apparatus for transmitting a high intensity beam of light such a laser beam, comprising:

an optical fiber having a light receiving end and a light emitting end a forward end protecting cover which is openably and closably provided at said light emitting end of said optical fiber to prevent contamination of said light emitting end; and means for supplying dry gas proximate to said light emitting end of said optical fiber and for maintaining the pressure of said gas to remove liquid and other foreign matter from the vicinity of said light emitting end, whereby deterioration of the light transmitting capacity of the optical fiber which would result in overheating is prevented, said pressure being maintained at the lowest level wherein liquid and other foreign matter may be removed.

2. An apparatus as in claim 1 wherein said cover is formed of a shape memory alloy storing a shape so as to open at a first temperature and close at a second lower temperature, whereby said cover will open when a high intensity beam of light is incident thereon, and close when it is not.

3. An apparatus as in claim 1 wherein a rear surface of said cover is made rough.

4. An apparatus as in claim 1 wherein a rear surface of said cover is painted black.

5. An apparatus as in claim 1 wherein said cover is formed in at least two portions.

6. An apparatus as in claim 5 wherein said cover is formed in a plurality of portions.

7. An apparatus as in claim 5 wherein said portions do not extend beyond said light emitting end of said fiber when said cover is open.

8. A light power transmission apparatus for transmitting a high intensity beam of light such as a laser beam comprising:
an optical fiber including an optical light conductor, an inner layer surrounding said conductor and an outer layer surrounding said inner layer to form a ventilation path within said inner layer, said outer layer having a hole therethrough;
a forward end protecting cover which is openably and closably provided at a light emitting end of said optical fiber;
means for feeding dry gas to said path via said hole; and
a gas pressure sensor for monitoring the pressure of said gas in said path.

9. An apparatus as in claim 8 wherein said cover includes a cylindrical attaching portion proximate said light emitting end for fixing said cover between said inner and outer layer and having a central opening through which said light conductor extends and a cap portion covering the light emitting end of said optical fiber.

10. An apparatus as in claim 8 wherein said cover is formed of a shape memory alloy storing a shape so as to open at a first temperature and close at a lower second temperature, whereby said cover will open when a high intensity beam of light is incident thereon, and close when it is not.

11. An apparatus as in claim 8 wherein a rear surface of said cover is made rough.

12. An apparatus as in claim 8 wherein a rear surface of said cover is painted black.

13. An apparatus as in claim 8 wherein said cover is formed in at least two portions.

14. An apparatus as in claim 13 wherein said cover is formed in a plurality of portions.

15. An apparatus as in claim 13 wherein said portions do not extend beyond the said light emitting end of said fiber when said cover is open.

16. An apparatus as in claim 8 further comprising a laser for supplying light to said fiber.

17. A light transmission apparatus comprising:
an optical fiber having a light receiving end and a light emitting end; and
a metal cover mounted to said light emitting end and formed of a shape memory alloy storing a shape so as to open at a first temperature and close at a lower second temperature whereby said cover will open when a high intensity beam of light is incident thereon, and close when it is not.

18. An apparatus as in claim 17 wherein a rear surface of said cover is made rough.

19. An apparatus as in claim 17 wherein a rear surface of said cover is painted black.

20. An apparatus as in claim 17 wherein said cover is formed in at least two portions.

21. An apparatus as in claim 20 wherein said cover is formed in a plurality of portions.

22. An apparatus as in claim 20 wherein said portions do not extend beyond the said light emitting end of said fiber when said cover is open.

23. An apparatus as in claim 17 further comprising a laser for supplying light to said fiber.

24. An apparatus as in claim 17 wherein said fiber comprises a quartz fiber.

25. An apparatus as in claim 17 wherein said fiber comprises a crystalline fiber selected from the group consisting of silver halide, thallium halide and alkalai halide.

26. A method of transmitting a high intensity beam of light such as a laser beam comprising the steps of:
transmitting light through an optical conductor to a light emitting end of an optical fiber contained therein; and
feeding a dry gas chosen from the group consisting of dry gas, Ar and $N_2$, and has a relative humidity equal to or less than 40% through said conductor proximate to said light emitting end so that liquid and other foreign matter may be removed from the vicinity of said light emitting end, whereby deterioration of the light transmitting capacity of the optical fiber which would result from overheating is prevented.

27. A method as in claim 26 wherein said gas is fed at a pressure between 1.01 and 1.2 kg/cm$^2$.

28. A method as in claim 26 including the further step of heating a cover which is provided at said light emitting end and is formed of shape memory alloy with incident light to open said cover in response to incident light.

29. An apparatus as in claim 1 further including a laser for supplying light to said fiber.

30. An apparatus as in claim 1 wherein said fiber comprises a quartz fiber.

31. An apparatus as in claim 1 wherein said fiber comprises a crystalline fiber selected from the group consisting of silver halide, thallium halide and alkali halide.

* * * * *